United States Patent [19]

Tsao

[11] Patent Number: 5,658,877
[45] Date of Patent: Aug. 19, 1997

[54] METHOD TO TREAT ENDOTOXIN EFFECTS BY ADMINISTRATION OF 33 KILODALTON PHOSPHOLIPID BINDING PROTEIN

[75] Inventor: Francis H. C. Tsao, Madison, Wis.

[73] Assignee: Wisconsin Alumni Research Foundation, Madison, Wis.

[21] Appl. No.: 443,511

[22] Filed: May 18, 1995

[51] Int. Cl.$^6$ ................................................ A61K 38/17
[52] U.S. Cl. ................................................ 514/2
[58] Field of Search ........................ 514/2, 12; 530/350

[56] References Cited

U.S. PATENT DOCUMENTS

| | | | |
|---|---|---|---|
| 5,201,308 | 4/1993 | Newhouse | 128/203.15 |
| 5,225,183 | 7/1993 | Purewal et al. | 424/45 |
| 5,238,683 | 8/1993 | Crystal | 424/434 |
| 5,298,489 | 3/1994 | Wallner et al. | 514/12 |
| 5,302,581 | 4/1994 | Sarin et al. | 514/12 |
| 5,314,890 | 5/1994 | Agostini et al. | 514/263 |
| 5,314,992 | 5/1994 | Guyre et al. | 530/350 |
| 5,316,915 | 5/1994 | Kraus et al. | 435/7.95 |
| 5,384,128 | 1/1995 | Meezen et al. | 424/450 |

OTHER PUBLICATIONS

Lacht et al. (1988) Am. J. Med. Sci. 296, 88–102.

Reutelingsperger et al., FEBS Letters 349 (1994), pp. 120–124 "Differential tissue expression of Annexin VIII in human."

Tsao FHC, et al., Biochim. Biophys. Acta 1213, 91–99 (1994) "Immunocharacterization and developmental regulation of rabbit lung calcium–dependent phospholipid–binding proteins."

Strijbos et al., Am. J. Physiol (1993) E289–E297, "Impaired febrile responses of aging mice are mediated by endogenous lipocortin–1 (annexin–1)".

Strijbos et al., Am. J. Physiol 263, (1992) E632–E636, "Inhibition of central actions of cytokines on fever and thermogenesis by lipocortin–1 involves CRF".

Das SK et al., Mol. Cellul. Biochem. 115, (1992) pp. 79–84, "Identification of calcium–dependent phospholipid–binding proteins (annexins) from guinea pig alveolar type II cells."

Keith et al., FASEB J. vol. 6 No. 4 Feb. 26, 1992, p. A1162, "Localization of phospholipid binding protein in rabbit lung".

Ambrose et al., American Journal of Respirory Cell and Molecular Biology, vol. 6 (1992) pp. 17–21, "Lipocortin I Production by Human Alveolar Macrophages."

Chung et al., Respiratory Medicine 85, 1991, 121–124 "Circulating autoantibodies to recombinant lipocortin–1 in asthma".

Perretti et al., Journal of Immunology, vol. 151, 1991 pp. 4307–4314, "Lipocortin–1 Fragments Inhibit Neutrophil Accumulation and Neutrophil–Dependent Edema in the Mouse".

Tsao FHC et al., "Lung calcium–dependent phospholipid––binding proteins: structure and function" Biochim. Biophys Acta 1081, 1991, 141–150.

Strijbos et al., American Journal of Physiological Society (1990) 11p, "Central and Peripheral Actions of Recombinant Lipocortin–1 and a Fragment of Lipocortin–1 on the Responses to Interleukin–1B".

Smith et al., Environmental Health Perspective vol. 85, 1990, pp. 135–144, "Detection of Lipocortin 1 in Human Lung Lavage Fluid; Lipocortin Degradation As a Possible Proteolytic Mechanism in the Control of Inflammatory Mediators and Inflammation".

Tsao FHC, Biochimica et Biophysica Acta. 1045 (1990) p29–39, "Purification and characterization of two rabbit lung $Ca^{2+}$–dependent phospholipid–binding proteins".

Ambrose et al., Am. J. Respir. Cell Mol. Biol. vol. 3, 1990, pp. 349–353, "Corticosteroids Increase Lipocortin I in Alveolar Epithelial Cells".

Ambrose et al., Am. J. Respir. 1990, pp. 1668–1671, "Corticosteroids increase Lipocortin I in BAL fluid from normal individuals and patients with lung disease".

Carey et al., J. Physiol 1990, R266–R269, "Lipocortin 1 fragment modifies pyrogenic actions of cytokines in rats".

Sakata et al., The Journal of Immunology vol. 145, No. 1, 1990 387–396 "The Role of Lipocortin I in Macrophage––Mediated Immunosupression in Tumor–Bearing Mice".

Davidson J., et al. Br. J. Pharmacol. 102, (1991) pp. 7–9, "Antipyretic actions of human recombinant lipocortin–1."

Maridonneau–Parini, I, et al. J. Clin. Invest. 83, (1989) pp. 1936–1940, "Inhibtion of O2 generation by dexamethasone is mimicked by lipocortin I in alveolar macrophages."

Perretti, M. et al. Pharmacol. Res. 30, (1994) pp. 53–59, "Cytokines, glucocorticoids and lipocortins in the control of neutrophil migration."

Cirino, G. et al. Proc. Natl. Acad, Sci. USA. 86, (1989) pp. 3428–3432, "Human recombinant lipocortin 1 has acute local anti–inflammatory properties in the rat paw edema test."

Relton, J. K. et al. J. Exp. Med. 174, (1991) pp. 305–310, "Lipocortin–1 is an endogenous inhibitor of ischemic damage in the rat brain."

Chung, K. F., et al. Respir. Med. 85, (1991) pp. 121–124, "Circulating autoantibodies to recombinant lipocortin–1 in asthma."

Perretti, M., et al. Br. J. Pharmacol. 103, (1991) pp. 1327–1332, "A novel anti–inflammatory peptide from human lipocortin 5."

Smith, S. F., et al. 151(4), (1995) p. A484, "Comparison of lipocortin 1 in human bronchoalveolar lavage (BAL) cells ex vivo and in vitro."

Drost, E. M., et al. 151(4), (1995) p. A453, "Effect of lipocortin 1 (Lcl) on human polymorphonuclear neutrophil (PMN) deformability."

Tsao, F. H. C., et al. 151(4), (1995) p. A741, "Structure and function of annexin I in human bronchoalveolar lavage fluid."

*Primary Examiner*—Stephen Walsh
*Assistant Examiner*—Karen E. Brown
*Attorney, Agent, or Firm*—Quarles & Brady

[57] ABSTRACT

Pharmaceutical compositions containing safe and effective amounts of Annexin I or 33 kDa(PLBP) can be used in a number of methods for the benefit of animals.

2 Claims, No Drawings

METHOD TO TREAT ENDOTOXIN EFFECTS BY ADMINISTRATION OF 33 KILODALTON PHOSPHOLIPID BINDING PROTEIN

This invention was made with United States government support awarded by NIH, Grant # NIH Project #'s. HL 38744 and P50 HL46478. The United States Government has certain rights in this invention.

FIELD OF THE INVENTION

The present invention generally relates to annexins. More particularly, it relates to pharmaceutical compositions containing an annexin and methods of treating lung disease and endotoxin shock in animals, including humans.

BACKGROUND OF THE INVENTION

Annexins are a group of calcium-dependent, phospholipid-binding proteins. The calcium and phospholipid binding sites of most annexins are located in four repeated and highly conserved regions each of which contains about 70 amino acids. These proteins are widely distributed and at least nine members of the annexin family of proteins have been identified in mammalian tissues.

The lung is rich in annexins. Several members of the annexin family of proteins with apparent molecular weights ranging from about 32 to about 40 kDa have been isolated from lungs of animals. Annexin I, a 36 kD phospholipid binding protein, 36 kDa(PLBP), appears to be the most abundant of the annexin family of proteins in the lung. There is about five times more Annexin I present in the lung than the related annexin 33 kDa phospholipid-binding protein, 33 kDa(PLBP).

Compared to the whole lung, the alveolar epithelial type II cells in which the pulmonary surfactant complex is synthesized, stored and secreted have higher expression levels of Annexin I. In addition to the intracellular localization of Annexin I in alveolar type II cells, this protein has been found in lung lavage fluids from human and animals. A likely source of the Annexin I in the lung lavage fluid is the alveolar type II cells.

Using an antibody to Annexin I, researchers have found Annexin I and a smaller protein in the bronchoalveolar lavage (BAL) fluid of patients with lung diseases. The smaller protein was found to be a proteolytic breakdown product resulting from the action of neutrophil elastase upon Annexin I in the patients' BAL fluid. The discovery of the Annexin I breakdown product in human BAL fluid samples is consistent with the report that the Annexin I N-terminal region is subject to cleavage by various proteases to yield breakdown products.

I have discovered that a breakdown product of Annexin I, which has a molecular weight of about 33 kDa (33 kDa(BP)), immunoreacts with anti-Annexin I antibodies. I also have discovered that 33 kDa(BP) is cytotoxic and that it is present in higher concentrations in the BAL fluid of patients with lung diseases, including cystic fibrosis (CF), and premature infants with chronic lung disease (bronchopulmonary dysplasia (BPD) than in normal humans. In addition, the BAL fluid of patients with lung disease contains less Annexin I than that of normal humans. Based on these and other discoveries, I have found that administering Annexin I or 33 kDa(PLBP) to lung disease patients can be beneficial to such patients. I also have made the further discovery that the administration of Annexin I or 33 kDa(PLBP) can be beneficial in the treatment of endotoxin toxicity and inflammation. The major pathogenesis of endotoxin toxicity leads to inflammation and septic shock.

Bacteria or bacterial products, such as endotoxin from gram-negative bacteria, activate host response during infectious and inflammatory processes. Endotoxin, also known as lipopolysaccharide (LPS) for its chemical structure consisting of a polysaccharide part and a hydrophobic lipid part, can induce a wide variety of different types of cells including macrophages, polymorphonuclear leukocytes, and endothelial cells to release a number of inflammatory mediators, such as prostaglandins or cytokines. In localized infections, endotoxin is largely restricted to inflammatory sites, enhancing host defense. However, if the infection is not brought under control, endotoxin and/or inflammatory mediators may reach the circulation, predisposing the microvasculature to thrombosis and can lead to systemic endotoxemia or sepsis and associated complications including septic shock, adult respiratory distress syndrome, and multiorgan failure.

Septic or endotoxin shock is an acute and serious cardiovascular collapse resulting from the systemic response to a bacterial infection. It is manifested by hypotension, a reduced response to vasoconstrictors, generalized tissue damage and multi-organ failure. It is the most common cause of death in the intensive-care unit; there are about 400,000 cases of septicemia per year in the United States with mortality rates between 25% and 50%. The steadily increasing incidence of septic shock stems from an increasing proportion of elderly in the population, increasing frequency of invasive surgical procedures, extensive use of immunosuppressive and chemotherapeutic agents, and increasing prevalence of chronic debilitating conditions. Because the mechanisms underlying sepsis and septic shock are not yet known, therapeutic interventions have been largely ineffective. At present, there is no effective treatment for septic shock.

It would be advantageous both to have methods of treating lung diseases, including cystic fibrosis (CF) and bronchopulmonary dysplasia (BPD), and treating endotoxin shock.

SUMMARY OF THE INVENTION

It is an object of the present invention to disclose novel pharmaceutical compositions containing annexins that can be used in methods of treating lung disease patients or in methods for treating patients with endotoxin shock.

The pharmaceutical compositions of the present invention comprise a member selected from Annexin I and 33 kDa (PLBP) and mixtures of those two polypeptides, in combination with pharmaceutical diluent(s) and excipients. The preferred compositions also contain a source of calcium ions ($Ca^{+2}$). Especially preferred for treating lung disease or endotoxin shock in animals are compositions which are suitable for instillation into the bronchial system of an animal.

In one method of the present invention, a composition containing a member selected from the group consisting of Annexin I, the 33 kDa(PLBP) and mixtures thereof, is administered to an animal having a lung disease in an amount which is safe and effective to improve the conditions of the lungs of said animal.

In another method of the present invention, a composition containing a member selected from the group consisting of Annexin I, the 33 kDa(PLBP) and mixtures thereof, is administered to an animal in an amount which is safe and effective to prevent or alleviate the adverse effects of endotoxin in said animal.

These and other objects of the invention will be apparent from the description and examples herein.

DESCRIPTION OF THE PREFERRED EMBODIMENT

The preferred pharmaceutical compositions are those which contain as the active ingredient the 33 kDa(PLBP). The reason that the 33 kDa(PLBP) is preferred is that it is as active as Annexin I both in the counteracting of the effects of endotoxin and in the treatment of lung disease and it is less likely to be broken down into cytotoxic products by enzymes.

In addition to the active ingredient and a source of calcium ions, the preferred compositions for instillation into the airway of an animal will contain a surfactant.

In the preferred methods of treating lung disease and preventing the adverse effects of endotoxin, the compositions are instilled directly into the patient's lungs. Therefore, the compositions also may contain pharmaceutical diluents and excipients which are customary for aerosols or other dosage forms for instillation of drugs into the airways of animals.

The practice of the present invention will be further understood by the description of the experimental work that follows.

Experimental Work

I. Degradation of Annexin I in Lung Disease

A study was conducted to determine whether degradation of Annexin I occurs in BAL fluid of patients with lung disease, such as cystic fibrosis (CF) and bronchopulmonary dysplasia (BPD). The lung disease of CF is characterized by bacterial infection and inflammation. As a result, the patient's mucus contains high amounts of proteases, particularly, the elastase from the neutrophils and from the organism *Pseudomonas aeruginosa* that colonized the respiratory tract of the CF patients. It was speculated that these proteases may break down proteins, including annexins, in the bronchi and bronchiole. The lung disease of premature infant BPD is characterized by oxyradical-mediated acute lung inflammation and injury. These premature infants survived respiratory distress syndrome (RDS) after intensive care but suffered oxygen toxicity and developed bronchopulmonary dysplasia, a chronic lung disease. The BAL fluid of these patients also contained high level of proteases derived from neutrophils in addition to the oxyradical substances. In this study, rabbit lung Annexin I, which is equivalent to human Annexin I, was used and specific antibodies were raised against rabbit lung Annexin I to analyze the distribution of Annexin I in BAL fluid from CF patients and BPD patients and to determine the changes in Annexin I structure and functional activity.

Isolation of lung annexins. Rabbit lung Annexin I was isolated from the cytosolic fraction of the lungs from two adult rabbits by known techniques. Human lung Annexin I was isolated from post-mortem lung tissue.

Isolation of lung annexins and preparation of anti-Annexin I antiserum. The two rabbit lung calcium-dependent phospholipid-binding proteins, Annexin I or 36 kDa(PLBP) and 33 kDa(PLBP), were isolated from cytosolic fraction of the lungs from adult rabbit by known techniques (Tsao FHC, Biochimica et Biophysica Acta. 1045 (1990) 29–39, incorporated by reference.) The 36 kDa (PLBP) was identified to be rabbit Annexin I (Tsao FHC, et al. Biochimica et Biophysica Acta. 1081 (1991) 141–150). Human lung Annexin I was isolated from post-mortem lung tissue by the same techniques. The purified rabbit lung Annexin I was used as antigen to raise specific antibodies in guinea pigs. The guinea pig antiserum to rabbit lung Annexin I (gpAb-Anx-I) was highly specific for rabbit lung Annexin I and cross-reacted with human Annexin I (Tsao FHC et al. Biochimica et Biophysica Acta. 1213 (1994) 91–99).

Analysis of annexin in bronchoalveolar lavage (BAL) fluid samples. Bronchoalveolar lavage fluid was obtained from normal volunteer subjects, patients with CF, patients with interstitial lung disease (ILD), and patients with bronchopulmonary dysplasia (BPD). The BAL fluids were concentrated 5 to 10-fold by centrifugation (3000×g at 4° C.) using Amicon Centricon10 filters (molecular weight cut-off of 10 kDa) (Beverly, Mass.). Fluid retained by the filter was saved for further analysis. An aliquot of BAL fluid sample containing 0.1 mg of total proteins was lyophilized in Speed Vac (Savant Instruments, Inc., Farmingdale, N.Y.) to dryness. The sample proteins were resuspended in 20 µl of sample buffer containing sodium dodecyl sulfate (SDS) and denatured in boiling water for 5 min. The proteins were separated by SDS polyacrylamide gel electrophoresis (SDS-PAGE) under the denatured conditions using a vertical 10% SDS gel (7×8 cm). Proteins on the SDS gel were then electrophoretically transferred onto a nitrocellulose membrane. Annexins on the membrane were immunoblotted by the polyclonal antibody raised in guinea pig against rabbit lung Annexin I (gpAb-anx-I). As specified, in some studies proteins on the SDS gel were visualized by silver staining (Silver Staining Kit, Sigma Chemical Co, St. Louis, Mo.). The isoelectric point (pI) values of annexins in the BAL fluid samples with 50 µg of total proteins were determined by isoelectric focusing (IEF) using an IEF agarose gel with pH range between 3 and 10 (10×12.5 cm, FMC, Rockland, Me.). Proteins on the IEF gel were transferred to a nitrocellulose membrane by capillary force, and annexins on the membrane were analyzed by Western blot using gpAb-anx-I.

Effects of BAL fluid from CF patients on the activity and structure of Annexin I. An amount of purified rabbit lung Annexin I was incubated with CF BAL fluid samples in a ratio of 1 µg Annexin I/20 µg BAL protein in 10 µl of 0.01M Tris-HCl, pH 7.4 (for Western blot as described above), or in a ratio of 10 µg Annexin I/100 µg BAL protein in 50 µl of 0.01M Tris-HCl, pH 7.4 (for Annexin I activity measurement), at 37° C. for 1 h. The Annexin I activity was determined by measuring the aggregation of $^{14}$C-labeled phosphatidylcholine unilamellar liposomes to multilamellar liposomes by known techniques.

In a separate experiment, an amount of 0.2 mg of purified rabbit lung Annexin I was incubated with BAL fluid containing 0.42 mg total proteins in 0.3 ml of 0.01M Tris-HCl, pH 7.4, at 37° C. for 2 h. After reaction, the reaction mixture was centrifuged at 100,000×g for 10 min. Annexin I in the supernatant was isolated by HPLC C4 Vydac reverse phase as described above. The purity and the molecular weight of Annexin I obtained from HPLC reverse phase column were examined by SDS-PAGE and Western blot. The N-terminal sequence of Annexin I from HPLC reverse phase was determined using an automated Model 477A Liquid Pulse Sequencer and Model 475A Gas Phase Sequencer with on-line Model 120A PTH Analyzer and 610A Data Analysis System (Applied Biosystems, Foster City, Calif.).

Western blot analysis of annexins in human BAL fluid. With the use of 100 µg total BAL fluid proteins, Annexin I was detected in BAL fluid samples from normal volunteers by Western blot. Annexin I in one of the 10 normal volunteer BAL samples was only barely detected. Annexin I also was present in all 12 BAL fluid samples from patients with interstitial lung diseases. Small amounts of an immunoreacted protein with molecular weight around 33 kDa also was observed in some of the samples. This 33 kDa protein did not bind with phospholipid and was determined to be the 33 kDa(BP) breakdown product of Annexin I. It appeared that the BAL fluid samples of patients with interstitial lung disease which had about 20% neutrophil among total BAL fluid cells also contained small amounts of the 33 kDa(BP). In contrast, in 20 BAL fluid samples from CF patients, 17 samples had no Annexin I. In 11 of the 17 samples with no Annexin I, the only immunoreactive protein was the 33 kDa(BP). The other 6 among the 17 BAL fluid samples had no detectable immunoreactive proteins at all. Among the 20 CF BAL specimens, only three samples had Annexin I, but two of these three samples also contained the immunoreactive 33 kDa(BP). Interestingly, the three CF BAL samples which contained Annexin I also had lower neutrophil elastase activities. All the BAL fluids of CF patients contained neutrophils in concentrations over $10^5$ cells/ml, compared to the very low concentrations of neutrophils in normal volunteers and patients with interstitial lung diseases. The additional two BAL fluid samples from normal volunteers also contained Annexin I, but one of these two samples also contained the 33 kDa(BP).

Conversion of Annexin I to 33 kDa(BP) by CF BAL fluid and elastase. The incubation of purified rabbit lung Annexin I (1 µg) with four different CF BAL fluid samples (20 µg protein) yielded 33 kDa(BP) which was immunorecognized by the antibody. The 33 kDa(BP) was solely derived from substrate of rabbit lung Annexin I since the four CF BAL samples employed in the tests contained only 20 µg of total proteins in which little Annexin I and 33 kDa(BP) could be detected. Under the reaction conditions, three BAL fluid samples converted most of the Annexin I to the 33 kDa(BP), whereas one BAL fluid sample degraded less Annexin I to the 33 kDa(BP). Interestingly, that CF BAL fluid sample also contained both endogenous Annexin I and 33 kDa(BP), whereas the other three CF BAL samples used in the reactions had no Annexin I but only the 33 kDa(BP).

The Annexin I breakdown product, the 33 kDa(BP), generated by a CF BAL fluid sample had a basic isoelectric point value with pI at 8.5, which was markedly different from the pI of 6.0 of Annexin I or the pI of 5.5 of 33 kDa(PLBP). The $M_R$ values of Annexin I and 33 kDa(PLBP) and their structures were determined as described in the literature.

The incubation of purified rabbit lung Annexin I with CF BAL fluid samples in which Annexin I was absent resulted in a decrease in Annexin I activity in liposome aggregation. Contrarily, the incubation of rabbit lung Annexin I with a CF BAL sample in which endogenous Annexin I was present did not affect Annexin I activity.

Elastase also degraded rabbit lung Annexin I into the 33 kDa(BP) which was immunorecognized by gpAb-anx-I. The presence of phenylmethyl sulfonyl fluoride (PMSF) in the reaction solution totally inhibited the proteolytic hydrolysis of Annexin I catalyzed by elastase.

In the experimental work described Annexin I was present in all the BAL fluid samples from normal volunteers. The finding of Annexin I in BAL fluid from normal volunteers was consistent with the previous reports that Annexin I was present in lung lavage fluid from animals and humans. Little degradation of Annexin I was observed in the BAL fluid samples from normal volunteers. However, degradation of Annexin I appeared to be common in all the BAL fluid samples from CF patients. In most of the CF samples, Annexin I was completely degraded to 33 kDa(BP). Only a few CF samples contained any Annexin I, but even those samples also had the 33 kDa(BP) protein. Although Annexin I was present in all the BAL fluid samples from patients with interstitial lung diseases, some of the samples also contained the 33 kDa(BP) protein.

It is interesting to note that among the BAL fluid samples from patients with interstitial lung diseases, the appearance of 33 kDa(BP) was associated closely with relatively higher percentage of neutrophils in these samples. Since all the BAL fluid samples from CF patients contained abundant neutrophils, it was concluded that the degradation of Annexin I to the 33 kDa(BP) was associated with neutrophils. Likely, the higher the neutrophil elastase in the BAL fluid, the more degradation of Annexin I took place. For those CF BAL fluid samples which had low elastase activity, Annexin I was present in the BAL fluid. Thus, the breakdown of Annexin I in BAL fluid was associated closely with the degree of lung inflammation in the CF patients.

The proteolytic activity in the CF patients' BAL fluid further was confirmed by the degradation of purified rabbit lung Annexin I incubated in reaction mixtures containing CF BAL fluid. The breakdown product 33 kDa(BP) of rabbit lung Annexin I catalyzed by CF BAL fluid structurally was nearly identical to the human lung Annexin I breakdown product in the CF BAL fluid samples, i.e., same molecular weight and pI between 8.5–9.0. The Annexin I breakdown product 33 kDa(BP) protein had a pI value which was distinct from the lung 33 kDa(PLBP), which was an acidic pI of 5.5. Both rabbit lung Annexin I and 33 kDa(PLBP) aggregated negatively charged vesicles in a calcium-dependent manner, an important annexin functional activity. The degradation of rabbit lung Annexin I catalyzed by CF BAL fluid markedly reduced the Annexin I functional activity, in other words, the Annexin I breakdown product 33 kDa(BP) was functionally inactive in vesicle aggregation.

Although previous studies suggested that the degradation of Annexin I in BAL fluid from patients with lung diseases was due to the elastase hydrolytic activity, we found that the cleavage site of Annexin I was at the N-terminus Val-36, an elastase substrate specific cleavage site. Also the cleavage site of Annexin I was determined with rabbit lung Annexin I which was used as the substrate. Both rabbit lung Annexin I and human lung Annexin I have nearly identical amino acid sequences in this region. It also was determined that human lung Annexin I could be cleaved at Ser-37. This suggested that degradation of Annexin I could occur at more than one position at the N-terminus. It has been shown that the N-terminus of Annexin I can be cleaved at several positions by different proteases, such as cathepsin D, calpain or plasmin, which have been demonstrated to cleave human annexin I at Trp-12, Lys-26 or Lys-29, respectively. The N-terminus truncated Annexin I has been shown to either increase or decrease the binding affinity with calcium and phospholipid, depending on the N-terminus-truncated position. It has been demonstrated that the removal of 36 amino acids at the N-terminus of Annexin I by the proteases in CF patients' BAL fluid diminished the Annexin I functional activity in vesicle aggregation and fusion, indicating that the N-terminus is required for Annexin I functional activity.

The source(s) of Annexin I in BAL fluid are not known with certainty. It has been found that alveolar epithelial type II cells are rich in Annexin I. Though the role of Annexin I in the type II cell is not clear, it might be associated with lung surfactant and possibly secreted by type II cells. The pulmonary surfactant appears not only to be essential to stabilize alveoli from collapse at the lowest volume during expiration, it also may play an important role in mucociliary clearance in the respiratory tract. The abnormal surfactant phospholipid composition in the mucus of CF patients not only may contribute to the abnormal mucociliary transport, but it also may cause the collapse of terminal airways. The degradation of Annexin I in the BAL fluid in CF patients was not only a sensitive indicator of the high levels of neutrophils and elastase in the inflammatory lung, it also was an indication of the decreased anti-inflammatory activity due to the reduction of the levels of Annexin I in the lungs of these patients. Similarly, Annexin I in the BAL fluid samples from five BPD patients was all degraded to 33 kDa(BP). These patients had acute lung inflammation and injury.

From the foregoing, it was apparent that administering Annexin I or 33 kDa(PLBP) to patients with lung disease would be beneficial to such patients.

II. Isolation and Structural Determination of 33 kDa(BP)

The rabbit lung Annexin I, after incubation of Annexin I with CF BAL fluid at 37° C. for 2 h, was purified by HPLC reverse phase column. This Annexin I was eluted as a single peak at the 35-min elution time from the column. Some minor proteins, presumably from BAL fluid, were eluted earlier than Annexin I. The apparent molecular weight of this Annexin I was determined to be 33 kDa by SDS-PAGE. Thus, this annexin protein was designated as Annexin I breakdown protein, or 33 kDa(BP).

Amino acid sequence determination of 33 kDa(BP) add human lung Annexin I. The 15 amino acid residues determined for the sequence of the 33 kDa(BP) protein derived from rabbit lung Annexin I matched the amino acid sequence between Ser-37 and Leu-51 of human Annexin I whose entire amino acid sequence had been deduced from cDNA as described in the literature. Among the 15 amino acids, Thr-41 in human Annexin I sequence was replaced with Phe in the 33 kDa(BP) protein and Asp-47 in human Annexin I sequence could not be determined for the 33 kDa(BP) protein.

The results of Western blot also showed that the immunoreacted Annexin I in human BAL fluid had the same apparent molecular weight as rabbit lung Annexin I. The molecular weight of human Annexin I calculated from amino acid sequence deduced from cDNA is 38712.16. Recently, the rabbit Annexin I cDNA was cloned and sequenced; the deduced protein sequence has 346 amino acids with a calculated molecular weight of 38831.28, similar to the Annexin I of human, rat, mouse and guinea pig. The apparent molecular weight of rabbit lung Annexin I was 36 kDa as vigorously examined by SDS gel. The observed molecular weights of human Annexin I also have been reported to be around 35–37 kDa. The difference in molecular weights between the calculated and experimentally determined might be the result of protein charge effects on protein migration on SDS gel due to some post-translational modifications. To be consistent with the observed molecular weight, lung Annexin I is referred to as 36 kDa(PLBP) protein since Annexin I was analyzed mostly by SDS-PAGE and Western blot.

III. Inhibition of Endotoxin and Cytotoxicity by Annexin I and 33 kDa(PLBP)

i. In Vitro Study of Anti-Endotoxin and Anti-Cytotoxicity Activities of Annexin I and 33 kDa(PLBP).

I have discovered that the Annexin I and 33 kDa(PLBP) have a high affinity for binding to endotoxin or lipopolysaccharide (LPS) and that the binding is calcium dependent. Both Annexin I and 33 kDa(PLBP) effectively inhibited endotoxin stimulation on macrophage release of cytokines. Also, Annexin I and 33 kDa(PLBP) inhibited killing of cells by cytokines released by activated macrophages. Overall, Annexin I and 33 kDa(PLBP) prevented endotoxin toxicity.

In the same in vitro cytotoxic assay in which it was demonstrated that both Annexin I and the 33 kDa(PLBP) protein prevented the killing of cells by the breakdown product of Annexin I 33 kDa(BP).

ii. Annexin I and 33 kDa(PLBP) Inhibit Cytotoxicity of BAL Fluid from CF Patients and BPD Patients.

I have found that the BAL fluid from either CF patients or BPD patients killed cells to a certain extent. These BAL fluid samples contained the 33 kDa(BP) but had no Annexin I. I also discovered that when Annexin I or 33 kDa(PLBP) was added to the cell culture medium, these proteins protected cells from killing by the BAL fluid of CF or BPD patients.

iii. In Vivo Study of Annexin I Against Endotoxin.

In this experiment, 6 New Zealand white rabbits (40-days old) were anesthetized with Ketamine followed by injection of 2 ml of saline into the tracheas of two control rabbits, 2 ml of saline containing 0.2 mg LPS into two Endotoxin group rabbits, or 2 ml of saline containing 0.2 mg LPS and 0.2 mg purified rabbit lung Annexin I into two Endotoxin+ Annexin I group rabbits. Anal temperature of each rabbit was measured every half or one hour after injection.

A tracheal injection of LPS into rabbits induced response within one hour. The animals had body temperatures 2°–3° F. higher than the controls within 5 hours. The body temperatures of the rabbits returned to normal levels 6 and 7 hours after injection. The injection of a mixture of LPS-Annexin I-calcium delayed the effects of endotoxin more than 2 hours and reduced the degree of response. The rabbits that received Annexin I eventually developed fever 4 hours later after injection. This is probably due to only one level of Annexin I being tested versus a large dose of endotoxin and the removal or degradation of Annexin I in the airway and the residual endotoxin causing infection. The difference between the Control and the average of the Endotoxin and Endotoxin+Annexin I groups for all times 3 hours and after was −1.97 degrees F. (p-value<0.001) while the difference for these times between the Endotoxin and Endotoxin+ Annexin was 0.85 degrees F. (p-value 0.014). This indicates that, after a brief incubation period, the Endotoxin+Annexin I group had a significantly lower average temperature than the Endotoxin group.

All the rabbits used in the in vivo study (trachea injection of endotoxin, Annexin I and endotoxin, or saline) were normal rabbits and they had endogenous Annexin I. This shows that introducing additional exogenous Annexin I into the airway of even healthy rabbits can inhibit endotoxin toxicity. The quantity of Annexin I in the airway is important in protecting against endotoxin. Therefore, introducing exogenous Annexin I and/or 33 kDa(PLBP) into an animal's airway will enhance the animal's defense mechanism.

The Annexin I anti-endotoxin activity is probably due to Annexin I binding to the lipid-A moiety of LPS so the LPS can no longer bind to the host cell membrane to trigger cellular reactions that release infectious mediators. Annexin I may also bind to the epithelial cell surfaces to prevent LPS from anchoring on the cell membrane to initiate cellular reactions. All the results indicated that Annexin I and 33 kDa(PLBP) can effectively inactivate endotoxins. Moreover, since these compounds are natural products of the lung their administration into the airway of animals, including humans, has minimal or no side effects.

IV. Uses for the Annexin I Breakdown Product, 33 kDa(BP)

33 kDa(BP) is an endogenous cytotoxic substance which can be used in cell culture and animal models to study cytotoxicity and apoptosis in laboratories. Since endogenous 33 kDa(BP) is not easy to obtain, the commercial production of 33 kDa(BP) will be useful. 33 kDa(BP) can be readily made in bacteria by the recombinant DNA techniques. The post-translational modification of the protein is not a concern in synthesizing 33 kDa(BP) in bacteria since Annexin I charge modification occurs at the N-terminus which is depleted in 33 kDa(BP) anyway.

The presence of 33 kDa(BP) in the diseased or inflamed lung appears to be a critical endogenous apoptosis factor that causes epithelial cell death and lung injury. Thus, the Annexin I/33 kDa(BP) ratio in BAL fluid can be used as diagnostic tool to predict lung injury. I have discovered that Annexin I and/or 33 kDa(PLBP) can effectively inhibit the cytotoxic activity of the Annexin I breakdown product 33 kDa (BP).

The 33 kDa(BP) also can be useful in the development of new drugs to inhibit 33 kDa(BP) cytotoxic activity. Inhibition of 33 kDa(BP) cytotoxicity can lower a patient's susceptibility to lung inflammation and enhance the patient's recovery rate. The discovery of 33 kDa(BP) therefor permits specific inhibitors to be developed to inhibit cytotoxicity in the airways of patients with lung diseases and to lower a patient's susceptibility to lung injury. I have discovered that Annexin I and/or 33 kDa(PLBP) can effectively inhibit the cytotoxic activity of the Annexin I breakdown product 33 kDa (BP).

33 kDa(BP) and the ratio of 33 kDa(BP)/Annexin I in BAL fluid also can be used in a diagnostic kit to diagnose or predict lung injury by using a specific antibody to 33 kDa(BP) to detect the presence of 33 kDa(BP).

V. Analysis of Annexin I in Human Amniotic Fluid (AF)

I also have discovered that the presence of Annexin I and 33 kDa(BP) in amniotic fluid can be useful in diagnosing high risk pregnancies.

In four AF specimens from four patients with high risk pregnancies, Annexin I and 33 kDa(BP) were detected in two of the AF specimens, whereas two AF specimens contained no Annexin I but only 33 kDa(BP). It is likely that these latter amniotic fluid specimens contained proteolytic enzymes which hydrolyzed Annexin I to yield the 33 kDa (BP). In addition, preliminary data showed that the breakdown of Annexin I in amniotic fluid from patients with high risk pregnancy was similar to that in the BAL fluid from patients with lung inflammation. Elastase inhibitor (PMSF) prevented Annexin I degradation in the presence of elastase.

In addition, to using the analysis of the amount of Annexin I/33 kDa(PLBP) in amniotic fluid as a means to predict premature delivery, the administration of Annexin I and/or 33 kDa(PLBP) into the amniotic fluid will help to prevent the infections, effects of cytokines and prostaglandins which are the major causes of premature delivery. The mechanism of the infection in amniotic fluid is similar to that in the airway.

The preferred pharmaceutical compositions, in addition to the Annexin I, the 33 kDa(PLBP) or mixtures thereof, will contain a source of calcium ions. When intended for instillation into the lungs of an animal, they also will contain a surfactant or surface active agent.

The Annexin I and 33 kDa(PLBP) are natural proteins in the airway. Therefore, the side effects and toxicities of these proteins are expected to be minimal. Both human Annexin I and 33 kDa(PLBP) can be synthesized or produced by genetic engineering techniques.

The preferred source of calcium ions is a soluble calcium salt, such as calcium carbonate or calcium chloride. The amount of calcium ions in the compositions will depend upon the amount of active ingredient. The calcium ion concentration can range from zero where enough endogenous calcium is present to about 1 mM or more.

A preferred surfactant would be one that is known to be beneficial in the treatment of lung disease, such as that sold under the trademark SURVANTA by Ross Laboratories. Suitable surface active agents include both non-fluorinated surfactants and fluorinated surfactants known in the art and disclosed, for example, in British Patent Nos. 837465 and 994734 and U.S. Pat. No. 4,352,789.

Examples of other surfactants include:
Sorbitan trioleate,
Sorbitan mono-oleate,
Sorbitan monolaurate,
Polyoxyethylene (20) sorbitan monolaurate,
Polyoxyethylene (20) sorbitan mono-oleate,
Lecithins derived from natural sources
Oleyl polyoxyethylene ether,
Stearyl polyoxyethylene,
Lauryl polyoxyethylene ether, and
Oleyl polyoxyethylene ether.

The surfactants or surface active agents are generally present in amounts not exceeding 5 percent by weight of the total formulation. They will usually be present in the weight ratio 1:100 to 10:1 surface active agent: active ingredient, but the surface active agent may exceed this weight ratio in cases where the active ingredient concentration in the formulation is very low.

The particle size of the active ingredients should desirably be no greater than 100 microns diameter. Preferably, the particle size of a finely-divided solid powder should for physiological reasons be less than 25 microns and preferably less than about 10 microns in diameter. The particle size for inhalation therapy should preferably be in the range 0.5 to 10 microns.

The concentration of the active ingredient depends upon the desired dosage, but it is generally in the range 0.01 to 5% by weight. The dosage will usually be selected to bring the levels of the Annexin I or 33 kDa(PLBP) at least up to the levels of those polypeptides found in the lung or amniotic fluid of normal animals. It should be noted, however, that the dosage can be adjusted to any level which is tolerated without substantial adverse effect by the patient. Thus, dosages of from 0.05 µg/kg of the animal's body weight up to 500 mg/kg or higher could be used if such high levels are not toxic and produce the desirable result in the patient. The availability of an animal model for cystic fibrosis, mice homozygous for a disrupted CFTR gene, allows for the testing of compositions containing the active ingredients in animals without undue experimentation.

A representative composition for instillation into the lungs of animal would contain in 1 ml. about 0.02 mg of Annexin I or 33 kDa(PLBP); 0.5 mg of calcium (5 mM) and 0.4 mg of surfactant phospholipids. It could also contain other diluents and ingredients and it would be packaged in an aerosol form not requiring a CFC propellant. A composition for addition to amniotic fluid would not contain the surfactant.

From the foregoing, it will be apparent to those skilled in the art that this invention has wide and broad clinical applications for children and adults with cystic fibrosis, HIV/AIDS immune suppressed patients, neutropenic, post-operative, bed ridden and chronic obstructive pulmonary disease patients, as well as, infants with bronchopulmonary dysplasia and patients with septic shock or patients who have high risk pregnancies.

It will be apparent to those skilled in the art that a number of modifications and changes can be made without departing from the scope of the invention. Therefore, it is intended that the invention be limited only by the claims.

What is claimed is:

1. A method of treating an animal to prevent or alleviate the adverse effects of endotoxin in the lung, said method comprising administering into the airway of an animal a safe amount of 33 kDa(PLBP) which is effective to prevent or alleviate the adverse effects of endotoxin.

2. A method of claim 1 in which a surfactant is administered with the 33 kDa(PLBP) into the animal's airway.

* * * * *